United States Patent [19]
Zarling et al.

[11] Patent Number: 5,506,098
[45] Date of Patent: Apr. 9, 1996

[54] IN SITU HYBRIDIZATION METHOD

[75] Inventors: David A. Zarling, Menlo Park; Cornelia J. Calhoun, San Francisco; Elissa P. Sena, Palo Alto, all of Calif.

[73] Assignee: Daikin Industries, Ltd., Japan

[21] Appl. No.: 755,291

[22] Filed: Sep. 4, 1991

[51] Int. Cl.[6] .............................. C12Q 1/68; C12N 15/63
[52] U.S. Cl. ............................................. 435/6; 435/172.3
[58] Field of Search ...................... 435/6, 172.3; 935/76, 935/77, 78

[56] References Cited

U.S. PATENT DOCUMENTS

| | | | |
|---|---|---|---|
| 4,683,202 | 7/1987 | Mullis | 435/91.2 |
| 4,888,274 | 12/1989 | Radding et al. | 435/6 |

FOREIGN PATENT DOCUMENTS 8505685  12/1985  WIPO.

OTHER PUBLICATIONS

Infantolino et al. Biosis Abstract No. 89060272 Liver 9(6). 1989. 360–366.
Van Dekken et al. Biosis Abstract No. 89092972 J Cell Sci 94(2). 1989, 299–306.
Saiki et al., Science 230:1350–1354 (1985) "Enzymatic amplification of β–Globin genomic . . . ".
Honigberg et al., P.N.A.S. 83:9586–9560 (1986) "Ability of RecA protein to promote a search for rare . . . ".
Di Capua et al., J. Mol. Biol 157(1): 87–104 (1982) "Characterization of complexes between Rec–A protein . . . ".
Weier et al., Chromosoma 100:371–376 (1991) "Two–color hybridization with high complexity . . . ".
Fan et al., P.N.A.S. 87:6223–6227 (1990) "Mappling Small DNA sequences by fluorescence . . . ".
Griffith et al, J. Cell Biochem (Suppl. 13E, 287) (1989).
Koch et al, Chromosoma 98:259–265 (1989).
Haase et al, PNAS 87:4971–4975 (1990).

*Primary Examiner*—Margaret Parr
*Assistant Examiner*—Eggerton Campbell
*Attorney, Agent, or Firm*—Gary R. Fabian; Peter J. Dehlinger

[57] ABSTRACT

A method of identifying the presence of a known target sequence in double-stranded DNA contained in a fixed cellular or subcellular biological structure. By adding a stable, reporter-labeled RecA/single-stranded probe complex to the structure, the target sequence can be effectively labeled by in situ hybridization, allowing the target sequence to be visualized histologically and microscopically or detected by in situ cytometry or cell sorting flow techniques.

11 Claims, 6 Drawing Sheets

IN SITU HYBRIDIZATION METHOD

FIELD OF THE INVENTION

The present invention relates to a diagnostic method for performing in situ hybridization with double-stranded DNA targets.

REFERENCES

Alexandrov, S. P. M., et al., Chromosoma, 96:443 (1988).
Baan, R. A., et al., Prog Clin Biol Res 340A:101 (1990).
Blum, H. E., et al., Lancet, 771 (1984)Blum,
Blum, H. E., et al., Virology, 139:87 (1984)Blum,
Buchbinder, A., et al., J of Virol Methods, 21:191 (1988).
Chen, T. R., Cytogenet Cell Genet 48:19 (1988).
Cheng, S., et al., J. Biol. Chem. 263:15110 (1988).
Cherif, D., et al., Human Genetics 81:358 (1989).
Disteche, C. M., et al., Cytometry 11:119 (1990).
Emmerich, P., et al., Exp Cell Res 181:126 (1989).
Griffith, et al., Biochem. 24:158 (1985).
Haase, A. T., et al., Virology, 140:201 (1985).
Haase, A. T., et al., Proc Natl Acad Sci USA, 87:4971 (1990).
Harders, J., et al., EMBO J, 8(13):3941 (1989).
Joseph, A., et al., Exp Cell Res, 183:494 (1989).
Keller, G. H., et al., Anal. Biochem. 170:441 (1988).
Kitazawa, S., et al., Histochemistry, 92:195 (1989).
Korba, B. E., et al., Virology, 165:172 (1988).
Korenberg, J. R., et al., Cell, 53:391 (1988).
Lawrence, J. B., et al., Cell, 52:51 (1988).
Lawrence, J. B., Genome Analysis, 1:1 (1990).
Lebo, R. V., et al., Science, 225:57 (1984).
Lichter, P., et al., Science, 247:64 (1990).
Lichter, P., et al., Nature, 345:93 (1990).
Lucas, J. N., et al., Int J Radiat Biol, 56(1):35 (1989).
Madiraju, M., et al., Proc. Natl. Acad. Sci. USA, 85:6592 (1988).
McCormick, M. K., et al., Proc. Natl. Acad. Sci. USA, 86:9991 (1989).
Meyne, J., et al., Genomics 4:472 (1989).
Moyzis, R. K., et al., Proc Natl Acad Sci USA, 85:6622 (1988).
Narayanswami, S., et al., Cytometry, 11:144 (1990).
Niedobitek, G., et al., Am J of Pathology, 131(1):1 (1988).
Noonan, C. A., et al., Proc Natl Acad Sci USA, 83:5698 (1986).
Pinkel, D. et al., Proc Nat Acad Sci, 83:2934 (1986).
Shen, D., et al., Cancer Research, 48:4334 (1988).
Shibata, T., et al., J. Bio. Chem., 256:7557 (1981).
Simon, D., et al., Cytogenet Cell Genet, 39:116 (1985).
Trask, B., et al., Hum Genet 78:251 (1988).
Unger, E. R., et al., Am J of Surg Pathology, 10(1):1 (1986).
Urdea, M. S., et al., Nucl Acid Res, 16:4937 (1988).
van Dekken, H., et al., Acta histo, 37:91 (1989).
van Dekken, H., et al., Cytometry, 11:153 (1990).
van Dekken, H., et al., Cytometry, 11:579 (1990).
Weier, H., et al., BioTechniques 10(4):498 (1991).
Zischler, H., et al., Hum Genet, 82:227 (1989).

BACKGROUND OF THE INVENTION

In situ hybridization employs direct hybridization of a DNA probe with DNA or RNA in biological structures, typically permeabilized cells, subcellular fractions, or fixed chromosome preparations. Because the method can yield morphological information about the localization of specific-sequence target nucleic acid(s) in fixed biological structures, it is applicable to many areas of biomedical research, such as developmental biology, cell biology, genetics and particularly gene mapping, pathology and gene diagnostics.

In most applications, in situ hybridization is directed toward a target sequence in a double-stranded duplex nucleic acid, typically a DNA duplex associated with a pathogen or with a selected sequence in viral or cell chromosomal DNA. In this method, as it has been practiced heretofore, a single-stranded labeled probe is added to the permeabilized structure, which has been heated to a temperature sufficient to denature the target duplex nucleic acid, and the probe and denatured nucleic acid are allowed to react under suitable hybridization, or reannealing conditions. After removal of unbound (non-hybridized) probe, the structure is processed for examination for the presence of reporter label, allowing the site(s) of probe binding to target duplex nucleic acid to be localized in the biological structure, i.e., in the context of cell or subcellular morphology.

The method has been widely applied to chromosomal DNA, for mapping the location of specific gene sequences, and distances between known gene sequences (Lichter, Meyne, Shen), for studying chromosomal distribution of satellite or repeated DNA (Weier, Narayanswami, Meyne, Moyzis, Joseph, Alexandrov), for examining nuclear organization (Lawrence, Disteche, Trask), for analyzing chromosomal aberrations (Lucas), for localizing DNA damage in single cells or tissue (Baan) and for determining chromosome content by flow cytometric analysis (Trask). Several studies have reported on the localization of viral sequences integrated into host-cell chromosomes (e.g., Harders, Lawrence, Lichter, Korba, Simon). The method has also been used to study the position of chromosomes, by three-dimensional reconstruction of sectioned nuclei (van Dekken), and by double in situ hybridization with mercurated and biotinylated probes, using digital image analysis to study interphase chromosome topography (Emmerich).

Another general application of the in situ hybridization method is for detecting the presence of virus in host cells, as a diagnostic tool (Unger, Haase, Noonan, Niedobitek, Blum). In certain cases where the number of virus particles in the infected cell is very low, it may be necessary to first amplify viral sequences by in situ adopted polymerase chain reaction (PCR) methods (Haase, 1990, Buchbinder).

The in situ hybridization method described above has a number of limitations. The most serious limitation is the requirement for denaturing the duplex target DNA, to form the necessary single-stranded form of the target. Denaturation typically is performed by heating the sample or treating with chemicals and heat. The heat treatment can produce spurious and unwanted changes in the nucleic acid being examined, related to structural changes and nucleic acid reassociation with repeated sequences within the DNA. The repeated DNA sequences can randomly reassociate with one another. The step also adds to the time and effort required in the method.

Secondly, where the target sequence of interest is present in very low copy number, the method is limited, by renaturation kinetics, to long renaturation times. Even then, the method may be incapable of producing probe/target renaturation events at low target concentration. This limitation may be partly overcome, as indicated above, by first amplifying the target duplex in situ by modified PCR methods. However, the PCR approach involves additional steps, and may be unsuitable for many in situ studies, such as those involving localization of genomic chromosomal DNA sequences.

SUMMARY OF THE INVENTION

It is therefore a general object of the present invention to provide an in situ hybridization method, for use in detecting and/or localizing target duplex DNA in a fixed biological structure, which (a) does not require heat denaturation of the target duplex, and (b) is not limited in target duplex copy number by renaturation kinetics.

The present invention includes a method of identifying the presence of a known target sequence in a double-stranded nucleic acid contained in a cellular or subcellular biological structure, in a specific morphological relationship with the structure. The method includes adding to the structure, a probe complex composed of RecA protein stably bound to a single-stranded, reporter-labeled nucleic acid probe which is complementary to one of the strands of the duplex target sequence, under conditions in which the complex can contact the duplex nucleic acid. The complex is allowed to bind to the target sequence under non-denaturing conditions. After removing unbound complex, the structure is examined for the presence of the reporter-labeled probe bound to the nucleic acid.

The complex is preferably stabilized by preparation in the presence of ATPγS. The probe may be labeled with a detectable reporter, such as a radiolabel, enzyme or fluorescence tag, or with a ligand, such as biotin or digoxigenin, which can be subsequently reacted with a reporter molecule specific for the ligand, and carrying a detectable reporter.

In one general application, the method is used for detection and localization of genomic sequence(s) in fixed chromosome DNA structure(s) in metaphase spreads. In one embodiment, the microscopic ultrastructure of the chromosomes is determined, for example, by fluorescence microscopy, using fluorescence banding patterns. The location of the bound complex in relation to the known ultrastructure is then determined independently, for example, by a fluorescence-labeled probe complex whose fluorescence excitation wavelength is different from that of the chromosome banding fluorescence. Alternatively, fixed cells or cellular structures are probed in suspension followed by flow cytometric or microscopic analysis.

In another general application, the method can be used for detecting the presence of virus or integrated virus-specific genomic sequences in a host cell. The binding of a fluorescence-labeled probe to the virus sequence may be determined by fluorescent microscopy or fluorescence activated cell sorting (FACS) or a light or fluorescent or laser scanning microscope. Where an enzyme label is used a light microscope can be used to visualize colored (e.g., black) peroxidase product produced by the reporter enzyme.

These and other objects and features of the invention will become more fully apparent when the following detailed description of the invention is read in conjunction with the accompanying drawings.

DETAILED DESCRIPTION OF THE INVENTION

I. In situ Hybridization Method

This section describes the basic methodology of in situ hybridization, in accordance with the invention, as applied to various biological structures containing a duplex DNA target with a repeated or unique specific basepair sequence.

A. Preparation of Biological Structures for DNA Detection

The method of the invention is designed for detecting, by complementary-basepair hybridization, a selected target sequence in a biological structure contain a duplex nucleic acid, usually a DNA/DNA duplex nucleic acid. The biological structure is any morphologically distinct structure, such as a cell, sperm, parasite, subcellular fraction or chromosomal preparation containing the target nucleic acid.

The target duplex in the structure is typically chromosomal DNA, or nucleic acid duplex material associated with a viral, parasitic or bacterial pathogen, such as virus particles composed of viral duplex genome encapsulated or released from being encapsulated in viral coat proteins. Methods of preparing fixed biological structures, such as cells, nuclei, and chromosomal preparations generally follow those used in conventional in situ hybridization by DNA duplex denaturation and reannealing.

Briefly, the cellular compartment and DNA structure may be further fixed by treatment with an organic solvent and acid or cross-linking agent to fix the structural components in their natural morphological relationship. Common fixatives include acetic acid, salts, methanol, formalin, paraformaldehyde, and glutaraldehyde. After fixation, tissue sample may be prepared for slide presentation by embedding in wax or by freezing, followed by sectioning into thin slices.

More generally, the biological material is treated with one or more of a number of agents capable of deproteinizing and/or delipidizing the structures. Such methods can involve the use of proteases, lipases, acid, organic solvents including alcohols, detergents or heat denaturation or combinations of these treatments. A common treatment involves one or more washes with methanol:acetic acid.

Other pretreatments may be useful in reducing background, such as use of inhibitors of non-specific binding of nucleic acids. For example, prehybridization with non-specific carrier DNA (e.g. salmon sperm) or RNA (e.g. tRNA), may act to reduce non-specific probe binding to the fixed DNA-target structure.

Cellular structures of interest may be individual cells, obtained for example from cell culture, cells present in a tissue section or body fluid. Typically, cellular structures from a tissue are sectioned cryogenically, then treated on a slide, as above, to permeabilize the section, such as by treatment with methanol:acetic acid. Cellular structures may be studied to determine intracellular localization of genomic target sequence(s), or for detecting the presence and/or localization of an infective organism, such as virus, bacteria, or parasite in the cells.

Subcellular structures, such as nuclei and mitochondria, can be prepared by conventional fractionation methods, such as isopycnic centrifugation, to obtain subcellular material in enriched or substantially purified form. Thereafter, the enriched structure preparation may be permeabilized and deproteinized, as above, probed either in solution or affixed to a slide, as by drying.

Alternatively, the cells may be pretreated with 75 mM KCL, followed by treatment with methanol:acetic acid, to remove cytoplasm. This fraction, after purification may be further treated for probe hybridization. This method is illustrated in Examples 3–5 for the preparation of HEp-2 cell nuclei for in situ hybridization.

Briefly in these examples, HEp-2 cells were pelleted by low-speed centrifugation and the pellet was resuspended in 75 mM KCL for between 5 and 15 min for a desired amount of nuclear swelling to occur, followed by addition of ice cold methanol:acetic acid and centrifugation. After general further addition of ice cold methanol:acetic acid and gentle agitation of the cells after each addition followed by centrifugation, cytoplasm was degraded from the nuclei. The resulting isolated nuclei preparation was resuspended in methanol:acetic acid, placed in 10 µl aliquots on microscope slides, dried, and the slides stored at −20° C. for later use.

Another structure of general interest is a fixed chromosome preparation, typically derived from cells in metaphase (Pinkel, Cherif). The preparation may contain the entire set of genomic chromosomes from the cell, such as the preparation in FIGS. 1A and 1B, or individual, isolated chromosomes, such as can be obtained by published methods (Lebo, McCormick) or chromosome fragments. The chromosomes are generally treated with methanol:acetic acid, placed on a slide, then affixed to the slide with drying.

A variety of other subcellular structures, such as mitochondria, or pathogenic structures including parasites isolated from cell or blood samples, such as virion particles, may also be prepared according to standard methods, and fixed and permeabilized for in situ hybridization as above.

B. Target-Specific DNA Probe

The probe used in the method is a single-stranded nucleic acid, usually a DNA strand probe, or derived by denaturation of a duplex probe, which is complementary to one (or both) strand(s) of the target duplex nucleic acid. The probe sequence preferably contains at least 90–95% sequence homology with the target sequence, to insure sequence-specific hybridization of probe and target. The single-stranded probe is typically about 100–600 bases long, although a shorter or longer polynucleotide probe may also be employed.

The probe may be constructed or obtained by one of a number of standard methods. Many probes, such as various satellite DNA sequences are commercially available in single-stranded or double-stranded form. Other probes can be obtained readily from viruses, plasmids and cosmids or other vectors carrying specific sequences, by restriction digest of the vectors and electrophoretic isolation of the cut fragments if desired. Probes obtained in this manner are typically in double-stranded form, but may, if required, be subcloned in single-stranded vectors, such as an M13 phage vector.

Alternatively, the probe may be prepared in single-stranded form by oligonucleotide synthesis methods, which may require, for larger probes, forming subfragments of the probe, then piecing the subfragments together.

The probe is labeled with a reporter or ligand or moiety which allows detection of the targeted sequence in situ. For autoradiographic detection, the reporter is a radiolabel, such as $^{32}$P-labeled probe formed, for example by nick translation or polymerase chain reaction in the presence of labeled nucleotides.

For fluorescence detection, the probe may be labeled with one of a selection of fluorescence groups, such as FITC, BODIPY, Texas Red, or Cascade Blue which is excitable in a specific wavelength, such as 490, 540, and 361 nm. The groups are derivatized to 3' or 5' probe ends or by incorporation or reaction at internal positions, according to standard methods (Urdea, Keller, Zischler).

Alternatively, the probes may be labeled with a ligand-type reporter, such as biotin (Weier), digoxigenin (Zischler), or bromodeoxyuridine (BrdUrd) or other modified bases including fluorescein-11-dUTP (Boehringer-Mannheim) (Kitazawa). The probe reporter groups are detected, in situ, by reaction of the hybridized probe with a secondary reporter molecule which (a) binds specifically and with high affinity to the probe ligands, and (b) contains a detectable reporter. The binding moiety of the secondary molecule may be avidin or streptavidin, for binding to biotinylated nucleotides, anti-digoxigenin antibody, for binding to digoxigenin-labeled nucleotides, and anti-BrdUrd antibody for binding to BrdUrd-labeled probe.

The detectable reporter in the secondary molecule is typically a fluorescence label, but may also be a radiolabel, for autoradiographic detection, an antibody, an enzyme, for colorimeteric or chemiluminescence detection in the presence of a suitable substrate, or colloidal gold (Narayan-swami) for use in electron microscopic visualization.

C. RecA and mutant RecA803 protein purification:

RecA and RecA803 proteins, for use in forming the RecA/probe complex used in the invention, are preferably isolated from overproducing strains, such as E. coli strains JC12772 and JC15369 (obtained from A. J. Clark and M. Madiraju). These strains contain the RecA coding sequences on a "runaway" replicating plasmid vector present at high copy numbers per cell. The RecA803 protein is a high-activity mutant of wildtype RecA (Madiraju).

The RecA proteins can be purchased from Pharmacia or purified using fast protein liquid chromatography (FPLC) on a hydroxylapatite column followed by an anion (Mono Q) exchange column. The isolation procedure combines and modifies published procedures (Shibata et al., Griffith). Details are provided in Example 1.

The standard assays for monitoring the protein purification include assay of 38,000-dalton RecA protein by SDS-polyacrylamide gel electrophoresis (PAGE) (Pharmacia Phastgel system), enzyme assay of ssDNA-dependent ATPase activity using [$\gamma$-$^{32}$P] ATP and PEI cellulose thin-layer chromatography developed in a solvent of 0.5M LiCl and 0.25M formic acid, assay of DNase, assay of D-loop activity with 500-mer oligonucleotide probe.

Analysis of total protein from JC12772 and JC15369 cell extracts by SDS-PAGE (denaturing conditions) shows that the 38,000-dalton RecA protein is the major protein produced in these strains. The SDS-PAGE profiles of the final Mono-Q-purified RecA and RecA803 proteins showed a single 38,000-dalton band, free of other cellular polypeptides as detected by silver staining.

D. Preparation of RecA DNA Probe Complexes

The duplex nucleic acid in the biological structure of interest is reacted with a probe complex composed of RecA protein stably bound to the single-stranded probe. The complex is preferably prepared in a stabilized form in the presence of ATPγS.

RecA protein coating of probes is normally carried out as detailed in Example 2. Briefly, the probe, whether double-stranded or single-stranded, is denatured by heating at 95°–100° C. for five minutes, then placed in an ice bath for one minute followed by centrifugation at 0° C. for approximately 20 sec, before use. When denatured probes are not placed in a freezer at −20° C. they are usually immediately added to standard RecA coating reaction buffer containing ATPγS, at room temperature, and to this is added the RecA protein.

RecA coating of probe is initiated by incubating probe-RecA mixtures at 37° C. for 10 min. RecA protein concentration tested during reaction with probe varies depending upon probe size and the amount of added probe, and preferably ranges between about 5 to 50 uM. When single-stranded probes are RecA coated independently of their homologous probe strands, the mM and µM concentrations of ATPγS and RecA, respectively, can be reduced to one-half those used with double-stranded probes (i.e. RecA and ATPγS concentration ratios are usually kept constant at a specific concentration of individual probe strand, depending on whether a single- or double-stranded probe is used).

E. Probe Hybridization to Permeabilized Biological Structures

According to an important feature of the invention, sequence-specific binding of the RecA/probe complex to the target duplex contained in a biological structure is achieved by adding the probe complex to the structure, under non-denaturing conditions, i.e., below the denaturation temperature of the duplex DNA, and allowing the complex to contact the target duplex, typically for 1–4 hours at 37° C., until homologous binding of the probe complex to the target DNA sequence has occurred.

After probe binding to the target DNA sequence, the target structure is washed to remove unbound probe complex. In the usual case, where the probe reporter is a ligand, such as biotin, the washed structure is contacted with a detectable reporter molecule, such as fluorescence-labeled avidin (FITC-avidin), to bind a detectable reporter to the target-bound probe. The sample material is then further washed to remove unbound reporter molecule. A variety of wash procedures are suitable. The structure is visualized or otherwise viewed or detected by microscopy, fluorescence activated cell sorting, autoradiography, or the like, as for example described below.

The hybridization condition described in Example 3, for use in fluorescence-reporter detection of a biotinylated probe, are exemplary. Briefly, between 10–20 µl probe complex is applied to a fixed preparation on a glass slide. Glass coverslips are placed over the hybridization areas and sealed, and the reactions are incubated in a moist container in a 37° C. $CO_2$ incubator for between 1–4 hours. Following incubation, the coverslip rubber cement seal is removed and the slides, with coverslips are washed several times to loosen and remove coverslips and remove unbound probe complex.

The slides are placed in preblock solution, followed by (a) immersion in FITC (fluorescein isothiocyanate)-avidin, in preblock solution, then in several washes to remove unbound FITC-avidin. An antifade agent, with or without counterstain such as propidium iodide, may be used to reduce photobleaching. If necessary the probe signal may be amplified by reacting the material on the slide with biotinylated anti-avidin antibody, followed by several wash steps and addition of FITC-avidin, to enhance the amount of fluorescent signal bound to the target duplex.

The target structure is then examined for the presence of the reporter-labeled probe bound to the target nucleic acid, e.g., by fluorescence microscopy or laser scanning microscopy.

Figure 1A:
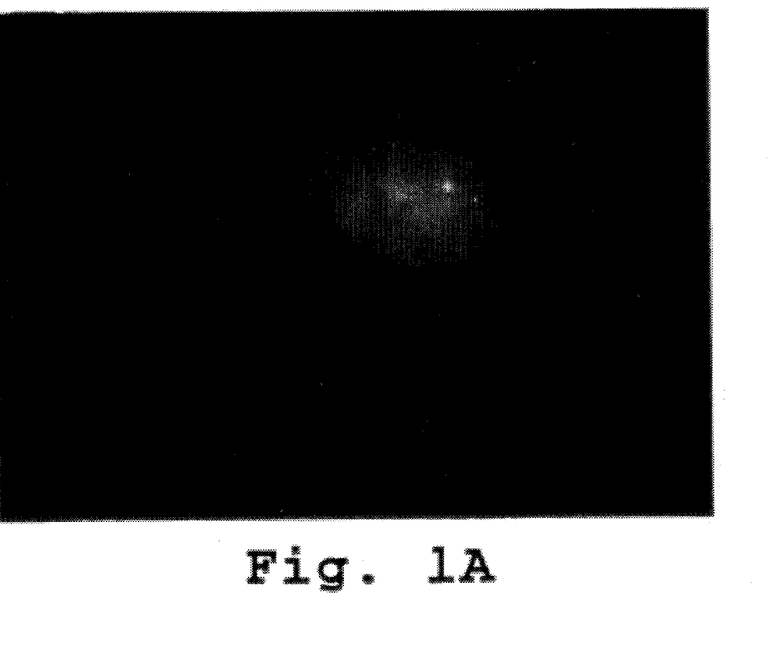
FIGS. 1A and 1B are fluorescence photomicrographs of chromosome X alpha satellite DNA probe used for detection of decondensed alpha satellite chromosomal centromeric DNA target sequences in native, nondenatured (1A) and heat-denatured (1B) methanol-acetic acid fixed interphase HEp-2 cell nuclei.

FIG. 1A shows FITC signal from in situ hybridization of a chromosome X alpha satellite DNA probe to prepared, isolated HEp-2 cell interphase nuclei fixed on glass slides, in accordance with the present invention and without amplification, following the protocol detailed in Example 3. chromosome X is estimated to contain about 5,000 copies/cell of the alpha satellite sequences (ONCOR literature). The biotinylated probe was reacted and post-labeled with FITC-avidin, as described above.

Figure 1B:
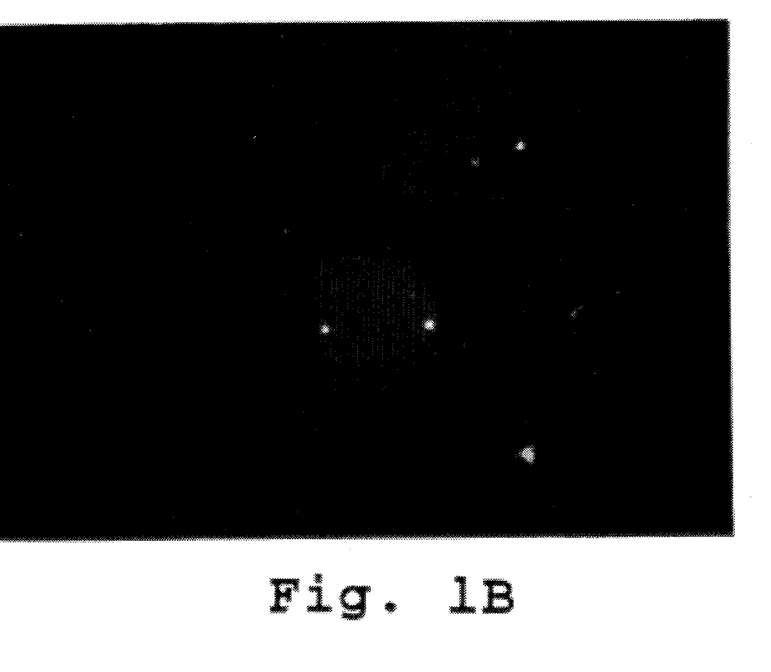

For comparative purposes, denatured biotinylated chromosome X alpha satellite probe from the same stock used in the FIG. 1A method was combined with formamide and dextran sulfate under traditional protocols and was hybridized to HEp-2 cell nuclei using prior art thermal denaturation (and renaturation) steps, with the results shown in FIG. 1B. The procedure required several more hours for total preparation and hybridization time than the FIG. 1A method, involved signal amplification, and generally gave a lower level of fluorescent signal through the nuclei.

A second method, reported in Example 4, shows that the method gives high-probe target specificity in a low copy number target sequence, without probe signal amplification. In this method, a chromosome-7 alpha satellite DNA/RecA complex is hybridized with HEp-2 interphase nuclei, as above. Chromosome 7 contains about 10 copies of the alpha satellite sequence probe used (ONCOR probe D7Z2).

Figure 2A:
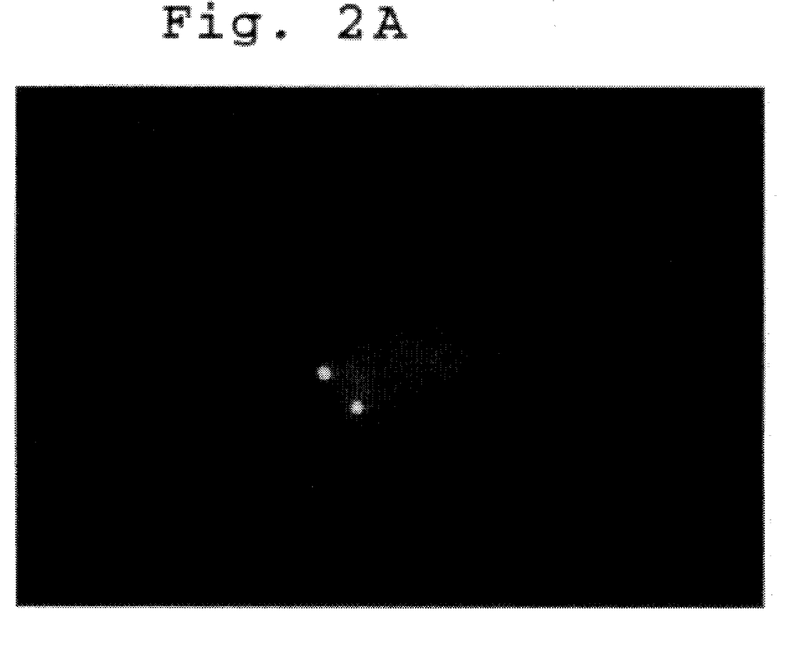
FIGS. 2A and 2B are fluorescence photomicrographs of alpha satellite DNA probe to chromosome 7 used for detection of decondensed chromosomal centromeric DNA target sequences in native, nondenatured (2A) and heat-denatured (2B) fixed nuclei in interphase HEp-2 cells.

FIG. 2A shows the target signal pattern after probe binding and FITC labeling, in accordance with the invention. As seen, the probe is localized in two distinct spots, presumably corresponding to the two chromosome 7's containing the alpha satellite sequence.

Figure 2B:
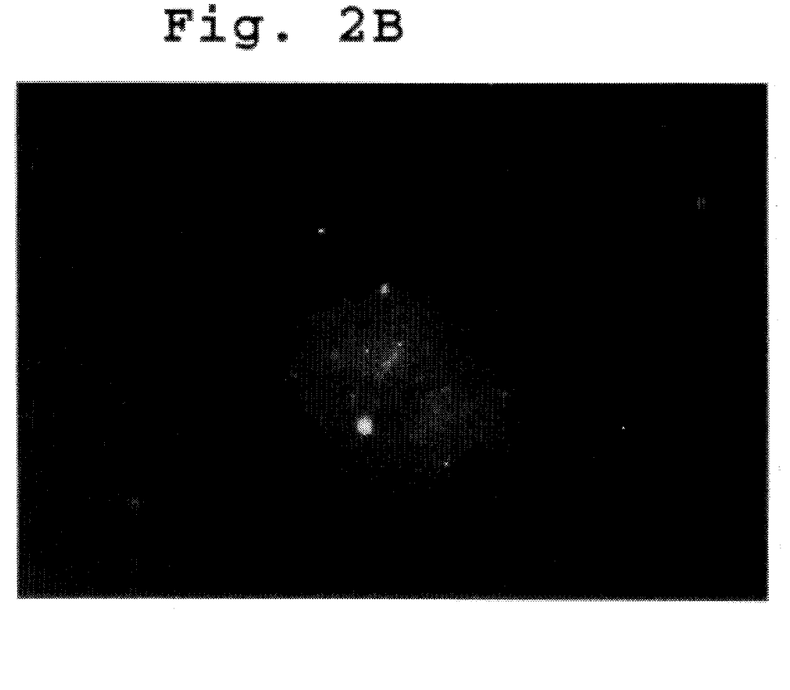

FIG. 2B shows the in situ hybridization probe bound target pattern achieved with the same probe, after amplification following prior art methods described above. Probe localization appears to be less specific than in the method of the invention. Further, total preparation and probe hybridization times were many hours longer.

Figure 3A:
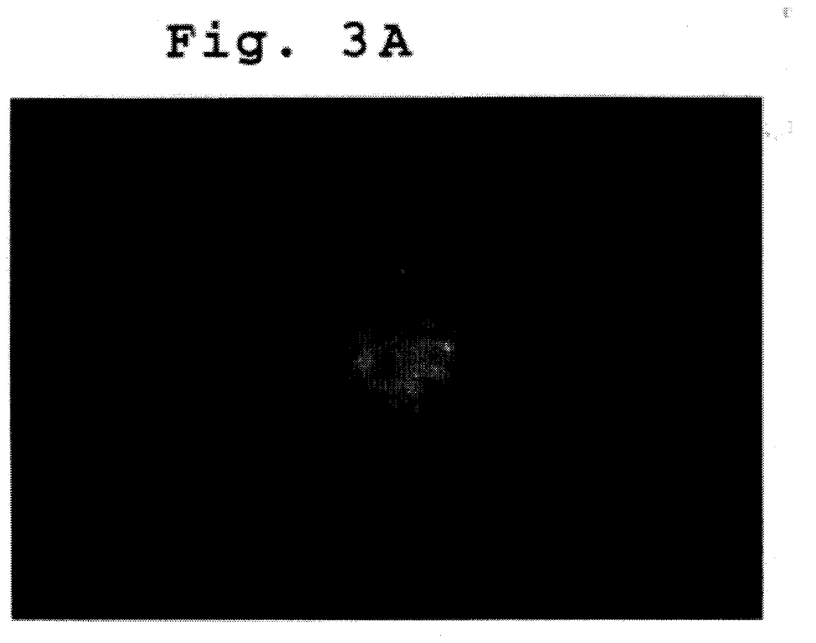
FIGS. 3A and 3B are photomicrographs taken under fluorescence microscopy (3A) and phase microscopy (3B), at the same focus, showing the distribution of chromosome X alpha satellite DNA in a dividing fixed HEp-2 cell nucleus.
Figure 3B:
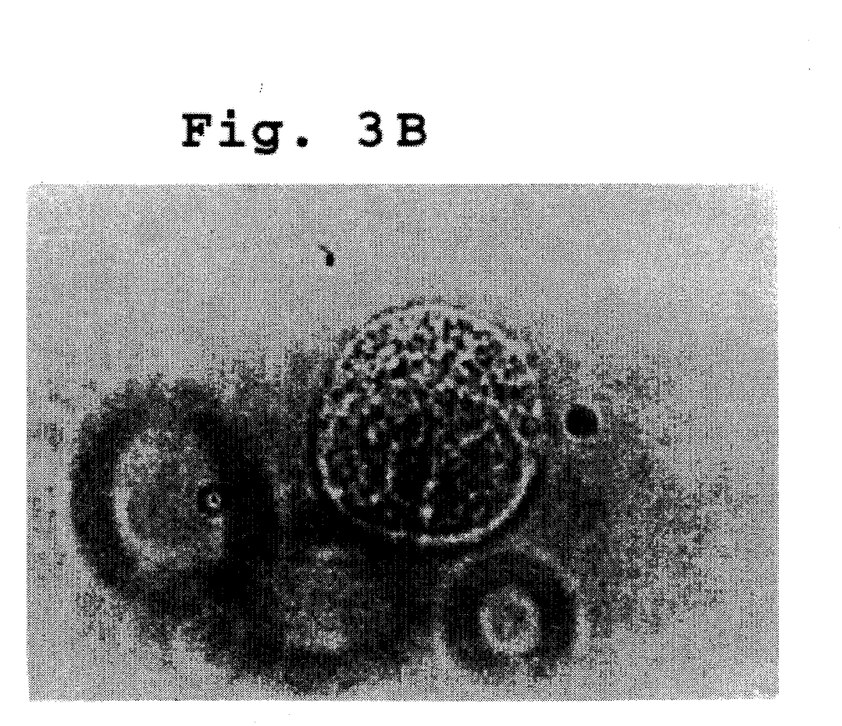

A third method, reported in Example 5, demonstrates the ability to localize a target sequence within a nuclear volume relative to other targeted DNA sequences and/or the nuclear membrane, using a confocal laser scanning microscope (Zeiss LSM-10). In this method, fixed HEp-2 nuclei were probed in suspension with the RecA/chromosome-X alpha satellite DNA probe complex, and labeled with FITC-avidin, as in FIG. 1A above. FIG. 3A shows the pattern of probe binding in a dividing nucleus. To localize the bound probe, the same field was viewed by phase contrast microscopy, without changing the focus of the lens (FIG. 3B). By examining the two photomicrographs, the relative position of the nuclear membrane and nuclear division plane can be seen with respect to the probe-labeled chromosomes.

From the foregoing, it will be appreciated how various objects and features of the invention are met. The invention provides a simplified and less time consuming procedure(s) for localizing target sequence in a biological structure. The method reduces artifacts by eliminating the need for a heat denaturation step and by reducing the need for signal enhancement, and allows more rapid and well defined detection of target sequences, including target sequences of low copy number.

In particular, the method allows detection of low-copy sequences without the requirement to first amplify the sequences. A comparison of FIGS. 2A and 2B demonstrate that this feature greatly enhances the specificity and resolution of the method over prior art approaches. Since most gene mapping and chromosomal studies are expected to involve specific low-copy sequences, the present method provides an important advantage for diagnostic gene mapping studies, as well as for diagnostic application involving unique or low-copy numbers of various pathogen sequences. These later applications are described in Section II below.

As disclosed in the co-owned patent application for "Diagnostic Applications of Double D-Loop Formation" filed on even date herewith, stable RecA-coated probes prepared from duplex DNA fragments can form double-probe hybrid structures with target duplex DNA. Although such double-probe structures have not been shown for probe binding under in situ hybridization conditions, the presence of such structures, if formed, could be exploited to effectively double the amount of signal produced at the in situ target site. Further, the two probes could be labeled with different reporter groups, for example, fluorescent probes with different absorption or emission peaks, so that target sites containing both probes could be distinguised from sites containing one probe only.

II. Applications

One general application of the invention is for diagnostic use in locating and visualizing a selected gene or regulatory sequence in a chromosome, and/or in a particular region of the chromosome. The target gene or sequence may be one which (a) generates a selected gene product, (b) is suspected of performing a critical cell-control function, such as that of a ribosome or an oncogene, (c) is related to a repeat sequence, (d) is suspected of containing a genetic defect which prevents expression of an active gene product, (e) may be related in chromosome position to a marker probe region with a known map position, and/or (f) may represent an integrated or non-integrated viral sequence in fixed chromatin or virions.

The diagnostic probe used in the method may be obtained, in some cases, from available plasmids, cosmids, viruses or other vectors, such as from human genomic libraries or may be chemically synthesized. Where the gene product is available, the probe may be generated by sequencing enough of the protein product to generate probes for PCR amplification, and amplifying and tagging the corresponding gene sequence in genomic DNA using the probes in a PCR format. The amplified gene material can be purified by electrophoresis and used directly as the probe, or cloned into suitable vectors, using standard protocols.

In a typical method, the nuclei are derived from cells staged in metaphase, using well known methods, then fixed and "dropped" on a glass slide to produce a metaphase chromosomal spread. Alternatively, the chromosome material under investigation may be a spread of an isolated individual chromosome(s).

Figure 4A:
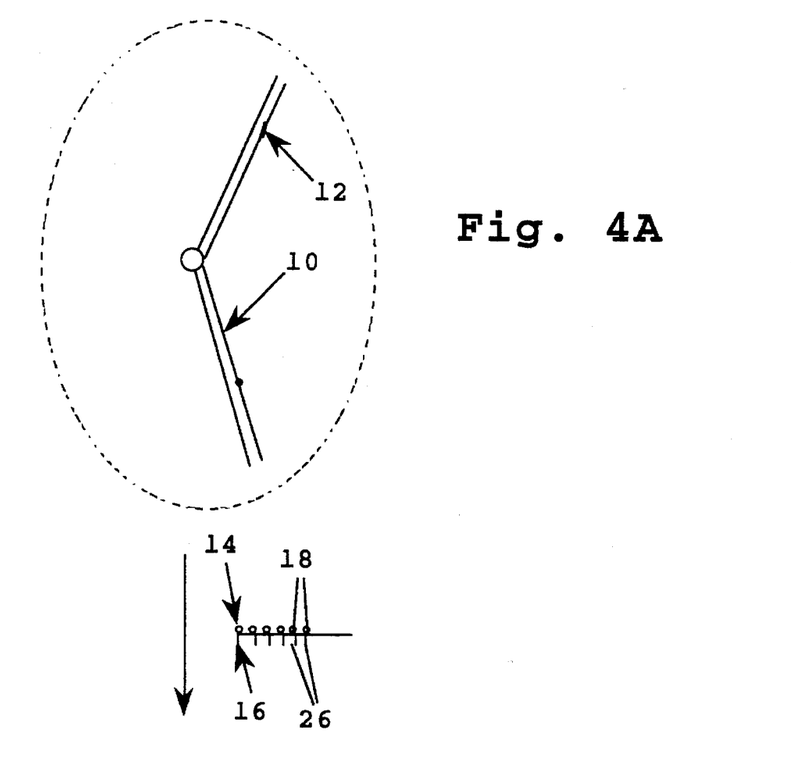
FIGS. 4A–4D illustrate steps for gene localization on a chromosome, employing the method of the invention.

FIG. 4A shows a single metaphase chromosome 10 which may be in isolated form or part of a field containing an entire set of somatic-cell chromosomes. The chromosome contains a known marker region 12 (gene site M) whose map location on the chromosome is known, and is suspected of containing a gene region of interest. The chromosome preparation on a slide is reacted with the probe complex, indicated at 14 in FIG. 4A, and composed of a probe 16 coated with RecA protein, shown by circles at 18, and having biotin groups, indicated by vertical dashes at 26. Reaction of the probe complex with the chromosome material, in accordance with the invention, leads to homologous binding of the probe to a gene site S (FIG. 4B) which is the target region of interest.

The binding site S may be visualized, for site localization by a variety of methods. In one method, illustrated in FIG. 4C, a second probe complex 22 composed of a probe 24 homologous to known region 12 (gene site M) and also containing biotin groups 26 is added to the chromosome preparation, and allowed to bind to its region of homology. After washing to remove unbound probe, the preparation is reacted with an FITC-avidin reporter 28, to label both sites on the chromosome with a fluorescent tag.

Figures 4B, 4C, 4D:
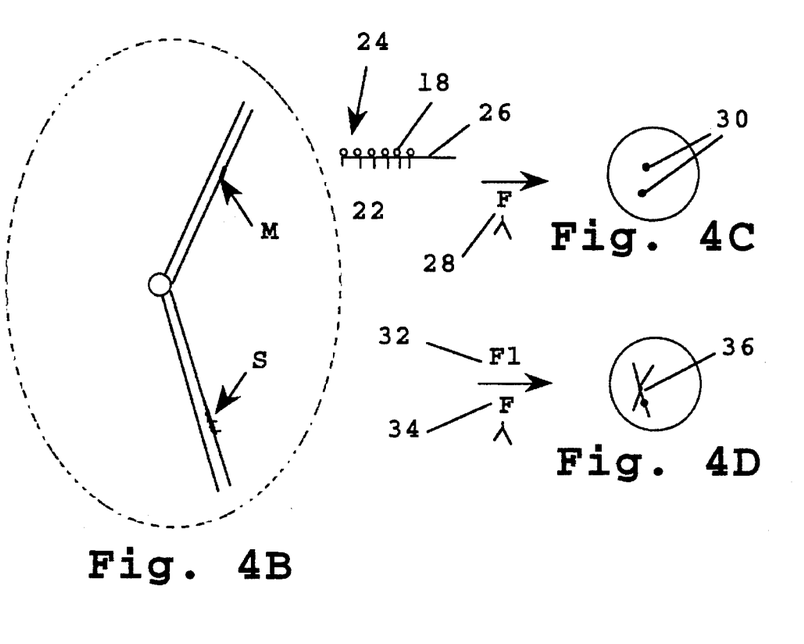

When viewed by fluorescence microscopy, a field such as shown at FIG. 4C is seen, with the two fluorescence points, shown at 30 in FIG. 4C, providing an indication of the distance between the marker and test sequences on the chromosomes.

In another visualization method, shown in FIG. 4D, the chromosomes are labeled with one or more specific fluorescent dyes, indicated at 32, which give characteristic staining patterns in metaphase chromosomes (Korenberg, Lawrence, 1990). The chromosomes are also labeled with an avidin reporter 34 containing a fluorescent label having a different fluorescence excitation wavelength from that of the band staining fluorescent molecule(s). Using fluorescence microscopy, the chromosomes are visualized at one wavelength, as indicated at 36 in FIG. 4D, and the location of the probe on the chromosomes site is visualized at a second excitation wavelength. Although reaction with one homologue is shown (4D) all homologous sequences would react with probe.

The invention also provides an improved method for detecting a variety of chromosomal abnormalities.

Figure 5A:
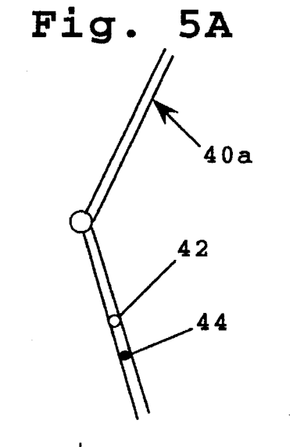
FIGS. 5–10 show various types of chromosomal aberrations (upper frames A), and the corresponding fluorescence pattern which would be seen with such aberrations (lower frames B)
Figure 5B:
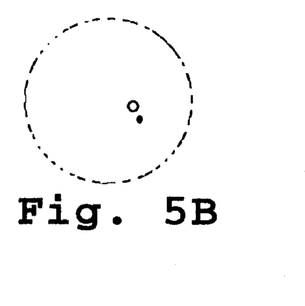

FIGS. 5–10 illustrate how the method can be applied to detecting various types of chromosome aberrations. FIG. 5, frame A shows a normal chromosome 40a containing two linked marker regions 42 and 44 on one of the chromosome arms. The two regions in the chromosome are hybridized with individual probe complexes, in accordance with the invention, then labeled with different fluorescent tags. For example, one of the regions may be labeled with an avidin-linked fluorescence reporter specific against biotin groups on one probe complex, and the second region, labeled with a second fluorescence reporter carried on an anti-digoxigenin antibody specific against digoxigenin groups on the second probe complex. The first and second fluorescence reporters are indicated by open and solid circles, respectively in FIG. 5 and in related FIGS. 6–10.

When the two regions are examined by fluorescence microscopy, at the appropriate excitation wavelengths, the two regions are localized by two distinguishable fluorescence spots (indicated by open and solid circles, in frame B). The two spots indicate the relative orientation of and distance between the two genomic regions in the normal chromosome.

Figure 6A:
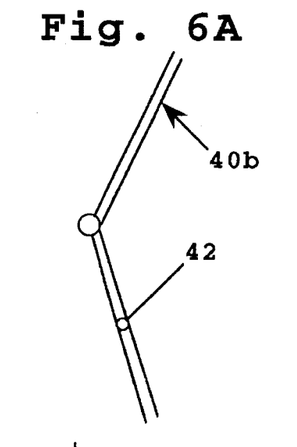
Figure 6B:
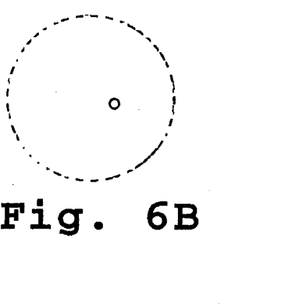

FIG. 6 illustrates, in frame A, a chromosome 40b which differs from chromosome 40a by a deletion of chromosome region 44. The mutation is seen, in frame B, as a single fluorescence spot at an excitation wavelength corresponding to region 42 only.

Figure 7A:
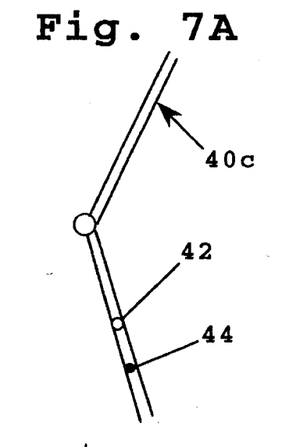
Figure 7B:
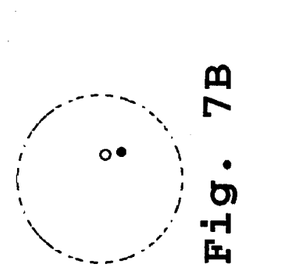

FIG. 7 illustrates, in frame A, a chromosome 40c which differs from chromosome 40a by an insertion between regions 42, 44 in the chromosome. The insertion is evidenced, in the fluorescence microscopy field seen in frame B, by a greater distance between the two fluorescence spots with respect to the FIG. 5 distance.

Figure 8A:
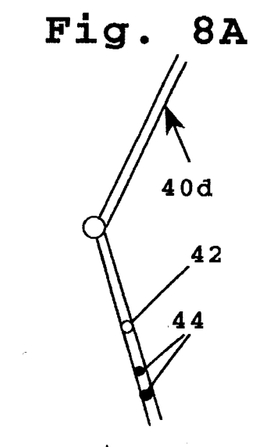
Figure 8B:
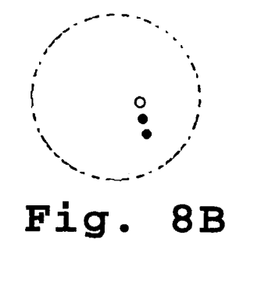

FIG. 8 illustrates, in frame A, a chromosome 40d which differs from chromosome 40a by a duplication of the region 44. The duplication is seen, in Frame B, as a doublet at the excitation wavelength of the region 44 probe, as indicated.

Figure 9A:
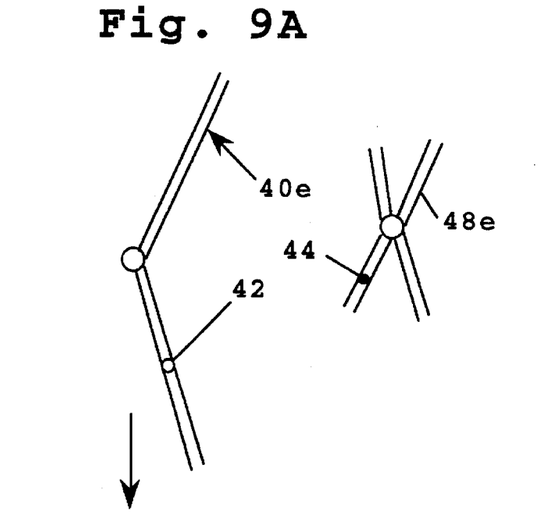
Figure 9B:
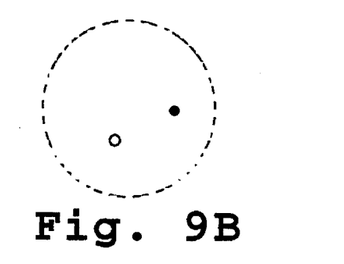

FIG. 9 illustrates, in Frame A, a chromosome 40e which differs from chromosome 40a in that a segment containing region 44 has translocated to a second chromosome 48e. The translocation is evidenced, in Frame B, by widely spaced fluorescence spots. The identity of chromosome 48e may be determined, as above, by staining the chromosomes with dyes which form characteristic metaphase banding patterns (or using chromosome 48 marker hybridization), as above.

Figure 10A:
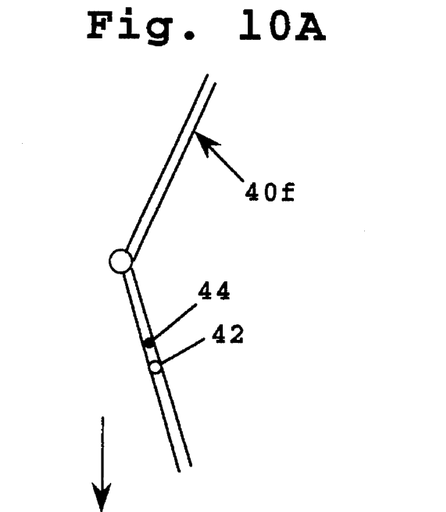
Figure 10B:
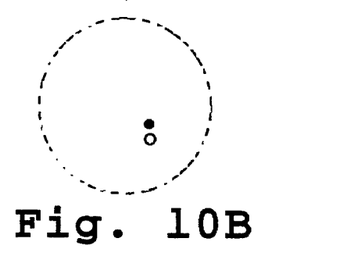

Finally, FIG. 10 shows, in frame A, a chromosome 40f which differs from chromosome 40a in that the segment carrying regions 42, 44 has been inverted. The inversion is evidenced, in Frame B, by reversal of positions of the two fluorescence spots.

It will be appreciated that the above applications of the method, to the extent they involve probe binding to a single or small-copy-number target sequence are uniquely suited to study by the present method.

Figure 11A:
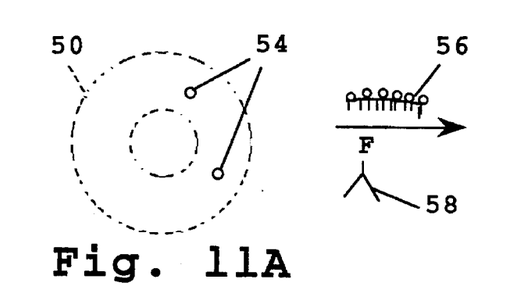
FIGS. 11A–11C illustrate the steps in detecting virus infection of cells, by fluorescence activated cell sorting, in accordance with the invention.
Figure 11B:
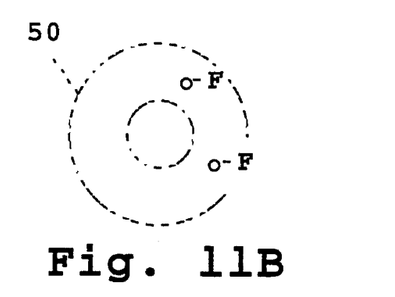
Figure 11C:
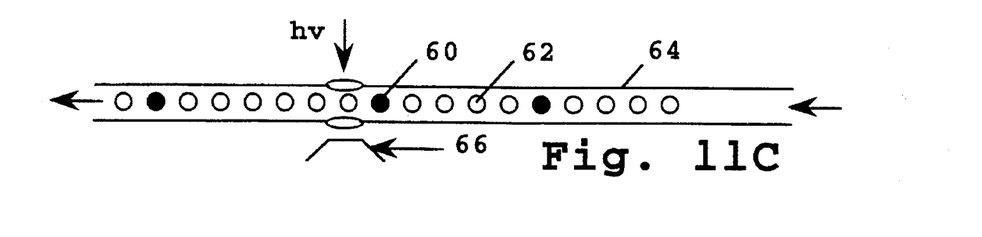

Another general application of the method of the invention is for diagnostics, typically for detecting changes in chromosome ploidy or rearrangement, or presence of a viral or bacterial or parasitic pathogen in an infected organism, organ, tissue, or cell. This application is illustrated in FIGS. 11A–11C for detection of virus infected cells, such as cell 50. Virion particles (or integrated viral genomes) contained in the cell are shown at 54. The cells, e.g., blood cells, are obtained from the test subject, and treated to permeabilize the cellular structures, as discussed above. To the permeabilized cells (FIG. 11A) is added a virus-specific DNA probe complex 56, with sequence specific binding of the DNA complex to virus duplex nucleic acid being followed by addition of a fluorescent marker molecule 58, for virus-complex labeling (FIG. 11B). The probe signal may be enhanced, if necessary, by the amplification of reporter reagents described above, e.g., a biotinylated anti-avidin antibody, followed by a second fluorescence-labeled avidin reporter molecule.

The labeled cells may be examined by fluorescence microscopy, to detect and localize infecting virus nucleic acid in the cells. Alternatively, cell infection, and percent cells infected, can be determined by fluorescence activated cell sorting (FACS), as illustrated in FIG. 11C. This figure shows a group of blood cells, such as cells 60, 62 passing through a capillary tube 64 in a FACS device equipped with a detector 66 for detecting fluorescence in individual cells passing through the detector region. Fluorescence labeled cells are indicated by dark shading in the figure. It is seen that the method provides rapid detection of infected cells, for diagnostic purposes, and is capable of measuring level of infection and percentage of cells infected. Thus, for example, the method can be used to assess the progress of an anti-virus treatment, by measuring decreases in cell infection over the treatment period.

The FACS device may be further equipped with sorting apparatus for capturing fluorescence-labeled cells, to form a concentrate of infected cells. The concentrate, in turn, can be used as a source of viral nucleic acid, for purposes of identifying and cloning the viral genome.

The following examples, which are intended to illustrate but not limit the invention, illustrate particular methods and applications of the invention.

EXAMPLE 1

Purification of RecA Proteins

RecA and RecA803 proteins were isolated from the overproducing strains JC12772 and JC15369 (obtained from A. J. Clark and M. Madiraju), or RecA was purchased from Pharmacia.

RecA and RecA803 proteins were purified by modification of published procedures (Shibata, Griffith) involving fast protein liquid chromatography (FPLC) using a hydroxylapatite column (obtained as powder from BioRad) followed by an anion ("MONO Q", Pharmacia) exchange column.

Protein purification was monitored as follows:

(i) identifying the 38,000-dalton RecA protein by SDS-PAGE ("PHASTGEL" system, Pharmacia, Piscataway N.J.);

(ii) assay of the RecA ssDNA-dependent ATPase activity using [$\gamma$S-$^{32}$P]ATP and single-stranded DNA (Shibata). The products of the reaction were separated using PEI cellulose thin-layer chromatography (EM Science, N.J.): the PEI plates were developed in a solvent of 0.5M LiCl and 0.25M formic acid. Products were detected by autoradiography.

(iii) assay of DNase activity. DNase activity was monitored by incubating the RecA protein samples with a mixture of $\phi$X174 linearized and supercoiled circular double-stranded RF and circular single-stranded DNAs in RecA strand-transfer buffer (Cheng) for 1 hr at 37° C. DNA nicking and digestion were monitored after deproteinization by visualizing the DNAs with ethidium bromide after agarose gel electrophoresis and comparing the quantities of each DNA type in the RecA incubated samples with those incubated in buffer without RecA. Only RecA protein samples showing no detectable DNase activity were used.

(iv) assay of D-loop activity with 500-mer oligonucleotide probe using a method modified from Cheng.

Silver stained SDS-polyacrylamide gel profiles of the final "MONO-Q"-purified RecA and RecA803 proteins showed a single 38,000-dalton band from each preparation that was free of other cellular polypeptides.

EXAMPLE 2

Preparation of Probe Complex

Biotinylated chromosome X alpha satellite DNA probe was obtained from ONCOR (Gaithersburg, Md.).

Probe diluted in sterile MilliQ (Millipore) H$_2$O was denatured in a 0.5 ml microcentrifuge tube in a 100° C. heat block for 5 min, and the tube immediately placed in an ice water bath. Approximately 5 min prior to addition of denatured probe to the hybridization mixture the tube containing the probe was placed in ice in a freezer at −20° C. The probe hybridization mixture contains the following components in a broad range of concentrations and is combined in the order listed: 1 ul of 10X RecA reaction buffer [10X RecA reaction buffer:100 mM Tris acetate pH 7.5 at 37° C., 20 mM magnesium acetate, 500 mM sodium acetate, 10 mM DTT and 50% glycerol (Cheng)); 1.5 ul ATPγS from 16.2 mM stock, (Pharmacia) (rATP or GTPγS may be used in some reactions); 0.75 ul 20 mM magnesium acetate; 4–60 ng (or more in some reactions) of denatured probe in sterile ddH$_2$O; RecA (when prepared in our own laboratory and the exact amount of μl added varies depending on concentration of stock, when purchased from Pharmacia, 1.25 ul 0.137 mM stock). The mixture was incubated at 37° C. for 10 min followed by addition of 0.5 ul/reaction of 200 mM magnesium acetate. Final concentrations of reaction components are: 4.0 mM to 10 mM Tris acetate, 2.0 mM to 15 mM magnesium acetate, 20.0 mM to 50 mM sodium acetate, 0.4 mM to 1.0 mM DTT, 2% to 5% glycerol, 1 mM to 2.5 mM ATPγS, 0.005 mM to 0.02 mM RecA.

EXAMPLE 3

In situ Hybridization with Chromosome X Probe

A. Preparation of HEp-2 Cell Nuclei

HEp-2 cells were originally derived from human male larynx epidermoid carcinoma tissue. HEp-2 is chromosome ploidy variable (Chen).

The cells were cultured for 24 hours after seeding in DMEM (Whittaker or GIBCO-BRL) supplemented with 10% FBS, sodium pyruvate and Penstrep antibotics mix at 37° C. under standard conditions. The cells were pelleted by low-speed centrifugation and gradually resuspended in 75 mM KCl in a 37° C. water bath, and allowed to incubate for between 5 and 15 min for the desired amount of nuclear swelling to occur, followed by addition of 3:1 ice cold methanol:acetic acid and centrifugation at 6° C.

One ml of fluid was left in the tube with the pelleted cells, additional ice cold methanol:acetic acid was added, and the cells suspended by gentle mixing of the tube, followed by centrifugation. Repeated additions of methanol:acetic acid degrades cytoplasm and isolated nuclei were obtained by repeated additions of methanol:acetic acid followed by mixing and centrifugation as above. (HEp-2 and other cell types may be fixed in alternative ways, some of which do not degrade fixed cytoplasmic structures).

Finally, the preparation of nuclei was resuspended in 3:1 methanol:acetic acid at a concentration about $2 \times 10^6$/ml and is either dropped by pipette in 10 μl aliquots onto clean glass slides which were stored at –20° C., or the suspended nuclei or cell preparation are stored at –20° C. for later use.

B. Nondenatured DNA Target-Hybridization Reaction

Ten μl of probe mixture/reaction from Example 2 was applied to the fixed preparation on glass slides. Glass coverslips were placed over the hybridization areas and sealed with rubber cement, and reactions were incubated enclosed in a moist container in a 37° C. CO$_2$ incubator for between 1–4 hours. Following incubation, the rubber cement was removed and the slides were washed in coplin jars 3 times for 10 min each in 2X SSC (20X SSC: 3M NaCl, 0.3M sodium citrate, pH 7.0 is used in all SSC containing preparations in these assays) in a water bath at 37° C. Other wash conditions may also be used.

The slides were placed in preblock solution [4X SSC, 0.1% Triton X-100, 5% Carnation nonfat dry milk, 2% normal goat serum (Gibco), 0.02% sodium azide, pH 7.0] for 25 min at room temperature (RT), followed by immersion in 5 ug/ml FITC-avidin DCS, cell sorter grade (Vector, A-2011) in preblock solution for 25 min at RT. The slides were washed in 4X SSC, 4X SSC and 0.1% Triton X-100, and 4X SSC for 10 min each at RT, followed by brief rinsing in double-distilled H$_2$O and dried. Antifade was applied [100 mg p-phenylenediamine dihydrochloride (Sigma P1519) in 10 ml PBS adjusted to pH 8 with 0.5M carbonate-bicarbonate buffer (0.42 g NaHCO$_3$ adjusted to pH 9 with NaOH in 10 ml ddH$_2$O) added to 90 ml glycerol, and 0.22 um filtered], and antifade mounting medium and coverslips were placed over the preparations. Antifade containing a counterstain such as propidium iodide or DAPI was sometimes used instead of antifade alone. FIG. 1A shows a fluorescence micrograph of a cell nucleus from the above preparation (no signal amplification).

If necessary, signal amplification may be performed as follows: Slides are washed for 5–10 min in 4X SSC and 0.1% Triton X-100 at RT to remove coverslips and antifade, followed by incubation in preblock solution for up to 20 min, then are incubated with biotinylated goat anti-avidin antibody (Vector BA-0300) at a concentration of 5 ug/ml diluted in preblock solution for 30 min at 37° C. Slides are washed for 10 min each in 4X SSC, 4X SSC and 0.1% Triton X-100, 4X SSC at RT followed by incubation in preblock solution for 20 min at RT, then immersed in preblock solution with 5 ug/ml FITC-avidin for 20 min at RT. Slides are again washed in the 4X SSC series, briefly rinsed in dd H$_2$O, and mounted with antifade or antifade with counterstain.

C. Hybridization by Heat Denaturation of the DNA Target

For comparative purposes, in situ hybridization by heat denaturation of nuclear substrate was performed in parallel. Denatured labeled X chromosome probe was added to the nuclei, denatured on a slide under ONCOR protocols. The same nuclear preparations were used as in the nondenatured method. The signal amplification procedure suggested by ONCOR was used to enhance the hybridization signal. Thereafter, the slide was maintained at 37° C. overnight. The procedures and materials generally followed that of the ONCOR Chromosome In situ Kit, Cat No. S1370.

FIG. 1B shows a fluorescence micrograph of a cell nucleus from the above signal amplified preparation.

EXAMPLE 4

In situ Hybridization With Chromosome 7 Probe

Biotinylated DNA probe to chromosome 7 alpha satellite DNA was obtained from ONCOR. The probe was denatured and could be stored frozen for at least five weeks. 32 ng of denatured freshly thawed DNA probe in 16 ul (1:2, probe:H$_2$O, 2 ng/ul DNA) were added to the same amount of hybridization mixture and in the same order given in Example 2. Following incubation of the probe mixture at 37° C. for 10 min and final addition of 0.5 ul 200 mM magnesium acetate, the reaction contained a total of 21 ul.

Probe was incubated on the nondenatured HEp-2 target cell nuclei (Example 3B) for 2.5 hours at 37° C. in a CO$_2$ incubator followed by washing, blocking, and FITC-avidin incubation exactly as described for probe to chromosome X in Example 3B. The time to conduct the experiment, including the ethanol series treatment of the slide was approximately 5 hours. FIG. 2A shows a fluorescence micrograph of a cell nucleus from the treated preparation.

For comparison, the nuclei were reacted with chromosome 7 probe under heat-denaturation conditions, as in Example 3C. Briefly, 5 ng denatured probe to chromosome 7 alpha satellite DNA was combined with hybridization buffer (Hybrisol Vl, ONCOR, as in FIG. 1B) and denatured using ONCOR protocols. 7 ul of the probe mixture was hybridized with HEp-2 cell nuclei for 16 hours and the reaction treated according to ONCOR protocols, including signal amplification. FIG. 2B shows a fluorescence photomicrograph of the treated denatured nuclei.

EXAMPLE 5

Detection of Specific Chromosome Sequences in Methanol:acetic Acid Fixed Interphase Nuclei in Suspension A probe specific for the X chromosome alpha satellite DNA, Oncor probe stock (also used in Example 2) was diluted and denatured at 100° C. for 5 min, immediately placed in an ice-water bath (for approximately 15 min) and stored in a −20° C. freezer briefly (about 5 min) before addition to the hybridization mixture. The hybridization mixture was combined in the following order (components, concentrations, and mixtures are described in detail in Example 2): 1 ul 10X RecA reaction buffer (see Example 2), 1.5 ul ATPγS (16.2 mM stock, Pharmacia), 0.75 ul magnesium acetate (20 mM stock), 12 ul of denatured probe (ONCOR) containing 60 ng in a 1:2 dilution in $H_2O$, RecA (0.137 mM stock, Pharmacia) (20 ng or more than 60 ng can also be used). The mixture was incubated in a 37° C. water bath for 10 min followed by addition of 0.5 ul 200 mM magnesium acetate.

HEp-2 cell nuclei prepared as described in Example 3A were stored in methanol:acetic acid 3:1 (or other appropriate solutions) at −20° C. at a concentration of approximately $2.5 \times 10^6$/ml. About 0.5 ml of the suspended nuclei ($1.25 \times 10^6$) were centrifuged in a TOMY centrifuge set at 6° C. in a 1.5 ml microcentrifuge tube and resuspended followed by centrifugation in 200 μl to 1 ml of 70%, 85% and 100% ice cold EtOH. After the final centrifugation and removal of 100% EtOH supernatant the pellet was resuspended in 200–500 ul 1X RecA reaction buffer at RT, and placed in a 0.5 ml centrifuge tube and centrifuged.

The completed probe mixture was mixed with the pellet, and the tube placed in a 37° C. water bath for 1.5–2.5 hours. Incubation was stopped by addition of 250 ul 2 X SSC (prewarmed to 37° C.) followed by centrifugation. The pellet was resuspended in 2 X SSC (prewarmed to 37° C.) and incubated for 5 min at 37° C. Following centrifugation the pellet was resuspended in 500 ul blocking solution at RT for 20 min, then centrifuged and resuspended in 10 ug/ml FITC-avidin in 100 ul blocking solution at RT for 20 min. The tube was centrifuged and 250 ul 4 X SSC mixed with the pellet, again centrifuged, and 250 ul 4 X SSC with 0.1% Triton X-100 mixed with the pellet and again centrifuged with 250 μl 4 x SSC all at room temperature. After a final centrifugation the pellet was mixed with approximately 20 μl antifade. Specific signal was noted in approximately 30% of the suspended nuclei. Note: Experiments using fixed whole cells and/or fixed nuclei and other concentrations of different washing components have shown 50–90% reaction.

The FIG. 3A photomicrograph shows a dividing fixed HEp-2 cell nucleus, as viewed by confocal laser scanning microscopy, illustrating the symmetrically located FITC-labeled probe-bound centromeric targets. The phase picture in FIG. 3B below was taken of the same nucleus without changing the microscope focus.

Although the invention has been described with respect to particular protocols and applications, it will be appreciated that a variety of changes and modifications may be made without departing from the invention.

It is claimed:

1. A method of identifying the presence of a known target sequence in a double-stranded nucleic acid contained in a fixed cellular or subcellular biological structure, in a defined morphological relationship with the structure, by in situ hybridization comprising adding to the structure, a probe complex composed of RecA protein stably bound to a single-stranded, reporter-labeled probe which is complementary to a duplex target sequence, under conditions in which the complex can contact the duplex DNA target, allowing the complex to bind to the target sequence under non-denaturing conditions, removing unbound complex from said structure, and examining the structure for the presence of the reporter-labeled probe bound to the nucleic acid.

2. The method of claim 1, wherein the complex is stabilized by the presence of ATPγS or GTPγS.

3. The method of claim 1, wherein said probe is labeled with a ligand reporter, and said examining includes adding to the structure, specific ligand molecule, including antibodies, effective to stably bind to said ligand, and having a detectable reporter group.

4. The method of claim 1, for detecting the presence in a host cell, of a pathogenic (foreign) target duplex nucleic acid sequence, wherein said complex is added to the cells under conditions of host cell fixation, and said examining includes detecting the presence of a probe-bound reporter in said fixed cells.

5. The method of claim 1, wherein said examining includes detecting a fluorescent reporter bound to the resulting hybrid using either microscopy or a fluorescence activated cell sorter.

6. The method of claim 1, for localizing a selected target duplex DNA sequence integrated into a host-cell genome, wherein said complex is added to the chromosomes of the cell, and said examining includes examining the chromosomes microscopically to determine the relative position of reporter-labeled probe in relation to chromosome ultrastructure.

7. The method of claim 6, wherein said chromosomes are labeled with one fluorescence reporter, said probe is labeled with a second fluorescence reporter, and said examining includes viewing the cells by fluorescence microscopy separately at wavelengths effective to excite fluorescence in each of the two reporters.

8. The method of claim 6, for localizing the target sequence in a selected chromosome, which further includes adding to the structure a second probe complex composed of RecA protein stably bound to a single-stranded, reporter-labeled nucleic acid probe which is complementary to a duplex strand in a known region of the selected chromosome, and said examining includes determining the relative positions of reporters associated with each of the two complexes.

9. The method of claim 8, wherein the first-mentioned complex and the second complex are labeled with different fluorescence reporters, and said examining includes viewing the cells by fluorescence microscopy separately at wavelengths effective to excite fluorescence in each of the two reporters.

10. The method of claim 1, which further includes amplifying the target duplex DNA in the structure prior to said adding.

11. The method of claim 1, which further includes amplifying the probe bound to the target by addition of polymerase, and all four nucleotides, where one of the nucleotides includes a detectable reporter group.

* * * * *